US005731160A

United States Patent [19]
Melief et al.

[11] Patent Number: 5,731,160
[45] Date of Patent: Mar. 24, 1998

[54] INDUCTION OF ANTIGEN SPECIFIC T-LYMPHOCYTE RESPONSES BY STIMULATION WITH PEPTIDE LOADED MHC CLASS I MOLECULES ON ANTIGEN PROCESSING DEFECTIVE MAMMALIAN CELL LINES

[75] Inventors: Cornelis J. M. Melief, Haarlem; Wybe M. Kast, Leiden, both of Netherlands

[73] Assignees: Rijksuniversiteit Leiden, Leiden; Seed Capital Investments (SCI) B.V., Utrecht, both of Netherlands

[21] Appl. No.: 888,943

[22] Filed: May 26, 1992

[51] Int. Cl.$^6$ .................... G01N 33/554; C12N 5/06; A61K 45/05

[52] U.S. Cl. .................... 435/7.24; 435/352; 435/355; 435/366; 435/375; 435/377; 436/501; 424/184.1; 424/93.71; 424/534

[58] Field of Search .................... 424/88, 89, 92, 424/534, 93.71, 184.1; 435/7.24, 240.1, 240.25, 352, 355, 366, 375, 377; 436/501

[56] References Cited

U.S. PATENT DOCUMENTS 5,314,813   5/1994   Peterson et al. .

OTHER PUBLICATIONS

Cerundolo et al. Nature: 345:449–452 May 1990.
Bruijn et al. Eur. J. Immunol: 22:3013–3020 Nov. 1992.
Parham P. Nature 346:793–795 Aug. 1990.
Cohen Science 262:841–843 Nov. 1993.
Culmann et al. Eur. J. Immunol. 19:2383–2386, 1989.
Kast et al. Immunology Letters 30:229–231, 1991.
Lanzavecchia et al. Science 260:937–944 14 May 1993.
Paul, W.E. Fundamental Immunology 1993 see pp. 977, 978, 1222, 1223, Sep. 12, 1997.
Askonas et al., "Cytoxic T-memory Cells in Virus Infection and the Specificity of Helper T Cells", *Immunology*, 45: 79–84 1982).
van Bleek et al., "Isolation of an Endogenously Processed Immunodominant Viral Peptide From the Class I H–2K$^b$ Molecule", *Nature*, 348: 213–216 (1990).
Rötzschke et al., "Isolation and Analysis of Naturally Processed Viral Peptides as Recognized by Cytotoxic T Cells" *Nature*, 348: 252–254 (1990).
Schumacher et al., "Peptide Selection by MHC Class I Molecules", *Nature*, 350: 703–706 (1991).
Falk et al., "Allele–Specific Motifs Revealed By Sequencing of Self–Peptides Eluted from MHC Molecules", *Nature*, 351: 290–296 (1991).
von Boehmer et al., "Distinct Ir Genes For Helper and Killer cells in the Cytotoxic Response to H–Y Antigen", *J. Exp. Med.*, 150: 1134–1142 (1979).
de Waal et al., "Cytotoxic T Lymphocyte Nonresponsiveness to the Male Antigen H–Y in the H–2D$^b$ Mutants bm13 And bm14", *J. Exp. Med.*, 158: 1537–1546 (1983).
Macatonia et al., "Primary Stimulation by Dendritic Cells Induces Antiviral Proliferative and Cytotoxic T Cell Responses in Vitro", *J. Exp. Med.*, 169: 1255–1264 (1989).

de Bruijn et al., "Peptide Loading of Empty Major Histocompatibility Complex Molecules on RMA–S Cells Allows the Induction of Primary Cytotoxic T Lymphocyte Responses", *Eur. J. Immunol.*, 21: 2963–2970 (1991).
Connolly et al., "Recognition by CD8 on Cytotoxic T Lymphocytes is Ablated by Several Substitutions in the Class I $\alpha 3$ Domain: CD8 and the T–Cell Receptor Recognize the Same Class I Molecule", *Proc. Natl. Acad. Sci.* 87: 2137–2141 (1990).
Salter et al., "A Binding Site for the T–Cell Co–Receptor CD8 in the $\alpha_3$ Domain of HLA–A2", *Nature*, 345: 41–46 (1990).
Kast et al., "Protection Against Lethal Sendai Virus Infection by In Vivo Priming of Virus–Specific Cytotoxic T Lymphocytes With a Free Synthetic Peptide", *Proc. Natl. Acad. Sci.*, 88: 2283–2287 (1991).
Melief, "Tumor Eradication by Adoptive Transfer of Cytotoxic Lymphocytes", *Adv. Cancer Res.*, 58: 143–175 (1992).
Ljundggren et al., "Host Resistance Directed Selectively Against H–2–Deficient Lymphoma Variants", *J. Exp. Med.*, 162: 1745–1759 (1985).
Kärre et al., "Selective Rejection of H–2 Deficient Lymphoma Variants Suggests Alternative Immune Defence Strategy", *Nature*, 319: 675–678 (1986).
Ljunggren et al., "Empty MHC Class I Molecules Come Out in the Cold", *Nature*, 346: 476–480 (1990).
Townsend et al., "Association of Class I Major Histocompatibility Heavy and Light Chains Induced by Viral Peptides", *Nature*, 340: 443–448 (1989).
Powis et al., "Restoration of Antigen Presentation to the Mutant Cell Line RMA–S by an MHC–linked Transporter", *Nature*, 354: 528–531 (1991).
Salter et al., "Impaired Assembly and Transport of HLA–A and –B Antigens In A Mutant TxB Cell Hybrid", *EMBO J.*, 5: 943–949 (1986).
Henderson et al., "HLA–A2.1–Associated Peptides From A Mutant Cell Line: A Second Pathway of Antigen Presentation", *Science*, 255: 1264–1266 (1992).

(List continued on next page.)

*Primary Examiner*—Anthony C. Caputa
*Attorney, Agent, or Firm*—Hoffmann & Baron, LLP

[57] ABSTRACT

Induction of an antigen-specific T-lymphocyte response in a T-lymphocyte culture, e.g. a primary cytotoxic T-lymphocyte (CTL) response, by loading antigen-presenting vehicles which carry empty MHC molecules with an antigen-derived T-cell-immunogenic MHC-binding peptide, culturing T-lymphocytes in the presence of the peptide-loaded antigen-presenting vehicles under specific T-lymphocyte response-inducing conditions. Optionally, an antigen-specific T-lymphocyte is isolated from the resulting culture and cultured. The process can be used for preparing CTL which are specific for viral or other foreign antigens, or CTL which are specific for autologous peptides. The process can also be used for the identification of peptides that are capable of binding to MHC and inducing a T cell response.

10 Claims, 9 Drawing Sheets

OTHER PUBLICATIONS

Esquivel et al., "RMA/S Cells Present Endogenously Synthesized Cytosolic Proteins to Class I–Restricted Cytotoxic T Lymphocytes", *J. Exp. Med.*, 175: 163–168 (1992).

Sijts et al., "Cytotoxic T Lymphocytes Against The Antigen–Processing–Defective RMA–S tumor Cell Line", *Eur. J. Immunol.*, 22: 1639–1642 (1992).

Attaya et al., "Ham–2 Corrects the Class I Antigen–Processing Defect in RMA–S Cells", *Nature*, 355: 647–649 (1992).

Merrifield, "Solid Phase Peptide Synthesis. I. The Synthesis of a Tetrapeptide", *J. Amer. Chem. Soc.*, 85: 1149–2154 (1963).

Kast et al., "Eradication of Adenovirus E1–Induced Tumors by E1A–Specific Cytotoxic T Lymphocytes", *Cell*, 59: 603–614 (1989).

Kast et al., "Cooperation Between Cytotoxic and Helper T Lymphocytes in Protection Against Lethal Sendai Virus Infection", *J. Exp. Med.*, 164: 723–738 (1986).

de Waal et al., "Regulation of the Cytotoxic T Lymphocyte Response Against Sendai Virus Analyzed With H–2 Mutants", *J. of Immunol.*, 130: 1090–1096 (1983).

Schumacher et al., "Direct Binding of Peptide to Empty MHC Class I Molecules on Intact Cells and In Vitro", *Cell*, 62: 563–567 (1990).

Neefjes et al., "Allele and Locus–Specific Differences in Cell Surface Expression and the Association of HLA Class I Heavy Chain With $\beta_2$–Microglobulin: Differential Effects of Inhibition of Glycosylation on Class I Subunit Association", *Eur. J. Immunol.*, 18: 801–810 (1988).

Elliott et al., "Naturally Processed Peptides", *Nature*, 348: 195–197 (1990).

Boog et al., "Stimulation With Dendritic Cells Decreases or Obviates the $CD4^+$ Helper Cell Requirement in Cytotoxic T Lymphocyte Responses", *Eur. J. Immunol.*, 18: 219–223 (1988).

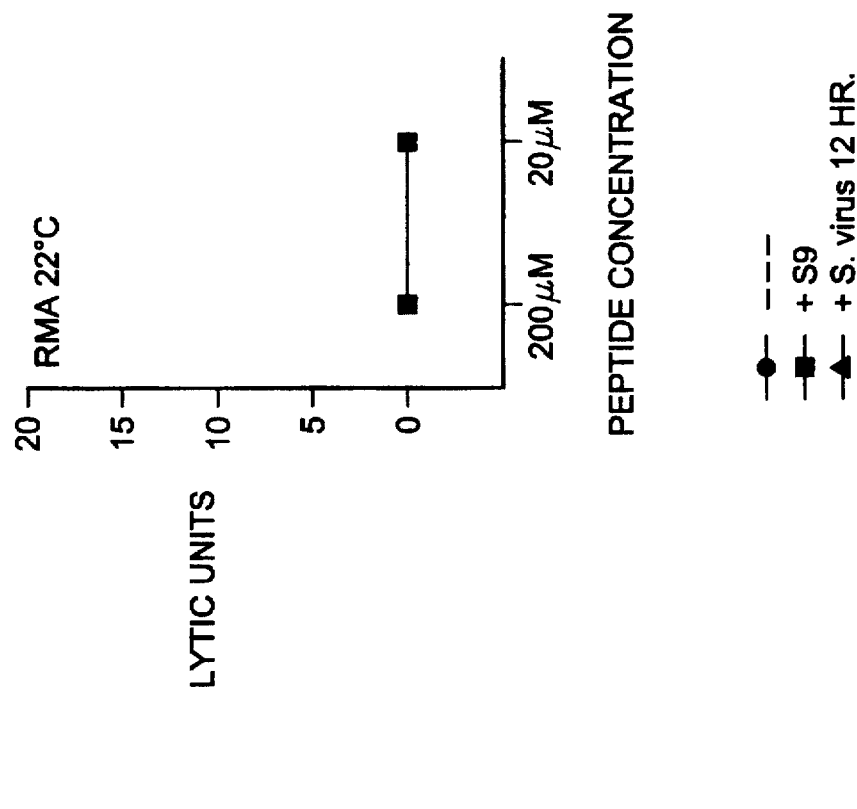
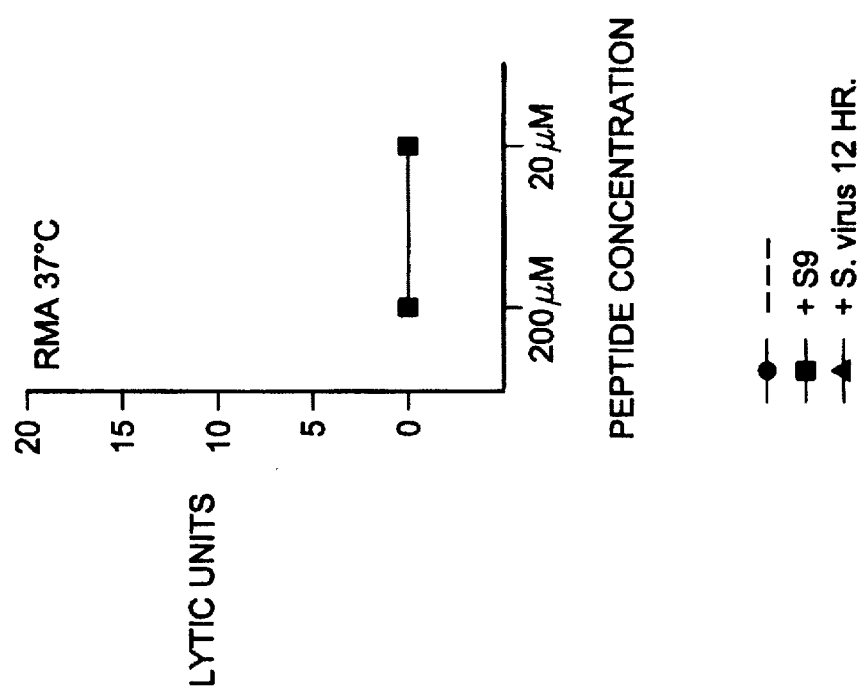

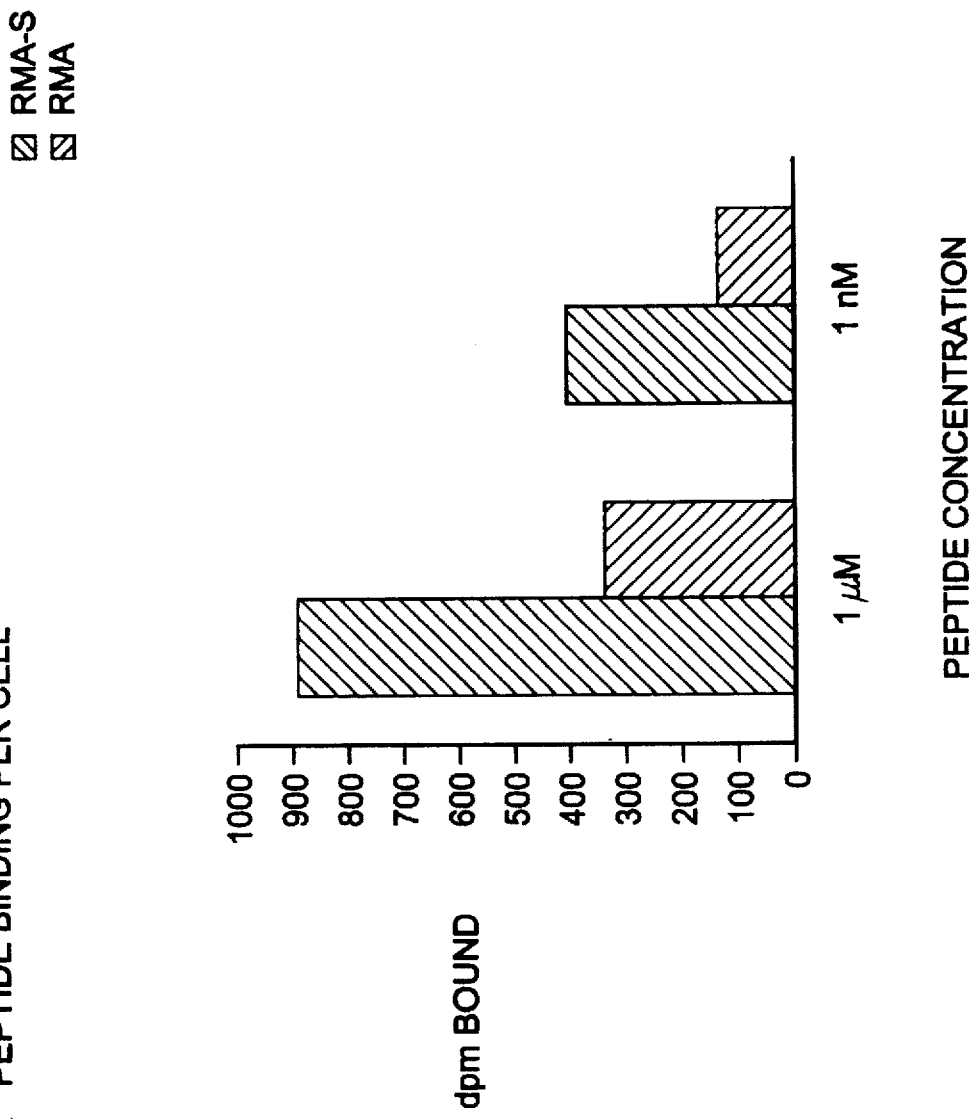

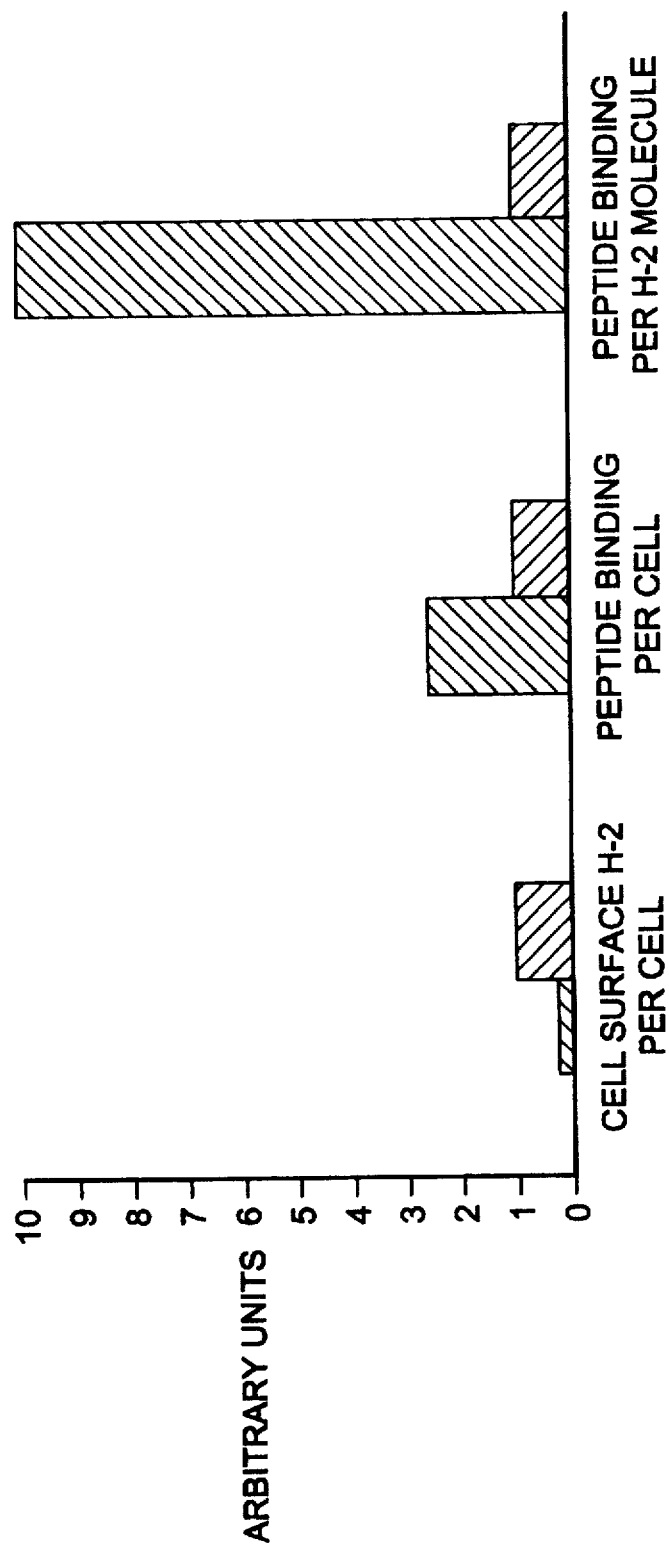

A. NWP SC
B. NWP SC + C'
C. NWP SC + anti-CD4/I-A$^b$ + C'
D. NWP SC + anti-CD4/I-A$^b$ + C' + anti-I-A$^b$ in culture

INDUCTION OF ANTIGEN SPECIFIC T-LYMPHOCYTE RESPONSES BY STIMULATION WITH PEPTIDE LOADED MHC CLASS I MOLECULES ON ANTIGEN PROCESSING DEFECTIVE MAMMALIAN CELL LINES

FIELD OF THE INVENTION

The invention is in the field of immunology and relates more in particular to a process which induces an antigen-specific T-lymphocyte response in a preferably naive culture of T-lymphocytes by treating them with appropriately presented antigen. Antigen-specific T-lymphocytes, especially antigen-specific cytotoxic T-lymphocytes (CTL) may be useful in pharmaceutical compositions for the protection of a mammal, usually a human being, against diseases caused by, e.g. a virus or a bacterium from which said antigen is derived. Antigen-specific T-lymphocytes may also be useful when they have specificity for an autologous antigen, for instance as a therapeutic agent against tumor cells which differ from normal cells by an increased expression of said autologous antigen or by expression of a mutant of said autologous antigen.

A peptide which is derived from either a heterologous or an autologous antigen and is capable of binding to a major histocompatibility (MHC) molecule located at the surface of an antigen presenting cell and is also capable of inducing a T-cell response, may also have utility in pharmaceutical compositions, either for vaccinating purposes or for therapeutic purposes. The invention relates to a process that can be used to identify such peptides.

BACKGROUND OF THE INVENTION

Initiation of antigen-specific T lymphocyte responses in vitro usually requires lymphocyte populations from immunized animals or human beings, because the precursor frequency of antigen-specific T-cells in naive (non-immunized) individuals is very low. For example in mice approximately one in $10^6$ total spleen cells or one in $3 \times 10^5$ splenic T cells is an antigen-specific CTL precursor (1). Therefore induction of antigen-specific T cell responses in vitro generally requires vaccination in vivo with antigen or antigen-pulsed (e.g. virus-infected) cells, followed by secondary restimulation in vitro. Bypassing of the need for in vivo immunization is desirable, especially for the generation of CTL responses against viruses and other antigens, such as tumor associated peptides, because it would allow rapid screening of peptides with proven binding ability to a given MHC class I allele for their capacity to induce CTL responses, without the requirement for vaccination. The invention aims at circumventing the need for in vivo immunization to identify MHC binding peptides that are capable of CTL response induction. Initiation of CTL responses requires recognition of small peptides, 8–11 amino acids in length, presented in the antigen presenting groove of MHC class I molecules to $CD8^+$ CTL precursor cells (2–5). Usually $CD4^+$ T-helper cells are required for optimal CTL responses (6, 7). Up till now, in vitro CTL response induction against virus-induced antigen presenting cells (APC) or viral peptide-loaded APC has only been successful with virus-infected or viral peptide loaded dendritic cells (DC) (8).

The purpose of the present invention is to provide a more convenient and reproducible method to induce T-cell responses, more particularly primary CTL responses against MHC class I binding peptides, without the need for in vivo immunization.

SUMMARY OF THE INVENTION

As indicated above, up till now in vitro CTL response induction against virus-induced antigen presenting cells (APC) or viral peptide-loaded APC has only been successful with virus-infected or viral peptide loaded dendritic cells (8). We found that peptide-loaded so-called "(antigen) processing" defective cells can also be used for that purpose. The latter methodology, first published by us (9), is the subject of the current patent application.

The crux of the invention is that the use of antigen processing defective cells leads to such an improvement of the stimulatory signal that primary peptide-specific CTL responses can now be induced from very low numbers of specific peptide-recognizing CTL precursors. The reason why the stimulatory signal is so much improved is that the effective specific peptide/MHC class I density on exogenous peptide-loaded antigen processing defective cells is much increased in comparison with parental cell lines without the antigen processing defect as illustrated in our publication (9) and in examples 1 and 2.

At the present time we have been able to induce primary CTL responses against both peptide-loaded murine processing defective RMA-S cells (9) and against peptide loaded processing-defective human T2 cells (Melief & Kast, unpublished observations).

An important reason why peptide-loaded processing-defective cell lines can and parental cells cannot induce primary peptide-specific CTL responses is that the former cells express more relevant peptide-loaded MHC class I molecules than the latter. A much larger concentration of peptide is required to initiate primary CTL responses than is needed for sensitization of target cells (9). In addition, it has been reported by others that the T cell receptor and CD8 molecules on the CTL must interact with the same MHC molecule filled with relevant peptide (10, 11).

The biologic relevance of peptide-induced primary CTL responses follows from the observation that peptide-induced primary CTL efficiently lyse virus-infected cells. Moreover vaccination with one of the peptides capable of primary CTL response induction, the Sendai virus 16-mer peptide HGEFAPGNYPALWSYA (see SEQ ID. NO.1), induces CTL memory in vivo, associated with protection against otherwise lethal Sendai virus doses (12). Similarly we have shown that viral peptide-specific CTL can eradicate large tumors (reviewed in 13 and 14).

The processing defective mutant murine cell line RMA-S expresses <10% of the amount of H-2 $D^b$ $K^b$ MHC class I heavy chains and β2 microglobulin at the cell surface at 37° C. in comparison with the parental line RMA (15, 16). Culture of RMA-S cells at reduced temperature (19°–33° C.) allows significant levels of cell surface expression of MHC class I molecules, only a few of which contain the endogenously derived peptides, the majority of these MHC molecules being empty (17). Those empty MHC molecules can be stabilised by addition of MHC binding peptides (18). Recent evidence has conclusively shown that this failure to load MHC class I molecules with endogenous peptides is due to a mutation in a peptide pump encoding gene, HAM-2, located within the MHC class II region (19).

In the absence of competition by endogenous peptides the empty MHC class I molecules can be filled efficiently and uniformly with an exogenous MHC class I binding peptide of choice. The level of MHC class I expression achieved by exogenous peptide incubation associated with MHC stabilisation never reaches the level of MHC class I on the parental cells. However, with respect to antigen presentation this is more than compensated by the uniform loading with a single immunogenic peptide (9).

The invention provides a process of inducing an antigen-specific T-lymphocyte response in a T-lymphocyte culture, comprising the steps of loading antigen-presenting vehicles which carry empty MHC molecules with an antigen-derived T-cell-immunogenic MHC-binding peptide, culturing T-lymphocytes in the presence of the peptide-loaded antigen-presenting vehicles under specific T-lymphocyte response-inducing conditions, and, optionally, isolating an antigen-specific T-lymphocyte from the resulting culture and culturing said isolated T-lymphocyte.

In a preferred embodiment, said antigen-presenting vehicles which carry empty MHC molecules comprise antigen-presenting cells having an antigen-processing defect.

It is also preferred that said antigen-presenting cells having an antigen-processing defect are loaded with peptide at a temperature of from about 20° C. to about 37° C.

More specifically, the invention provides a process of inducing an antigen-specific cytotoxic T-lymphocyte (CTL) response in a T-lymphocyte culture, comprising the steps of loading antigen-presenting vehicles which carry empty MHC Class I molecules with an antigen-derived T-cell-immunogenic MHC Class I-binding peptide, culturing T-lymphocytes comprising $CD8^+$ T-cell precursors in the presence of the peptide-loaded antigen-presenting vehicles under specific CTL response-inducing conditions, and, optionally, isolating an antigen-specific CTL from the resulting culture and culturing said isolated CTL.

Said antigen-presenting vehicles which carry empty MHC molecules preferably comprise antigen-presenting cells having an antigen-processing defect, such as murine RMA-S cells or human 174.CEM T2 cells.

Preferably, said antigen-presenting vehicles which carry empty MHC molecules in addition carry molecules which promote T-cell response initiation.

It is further preferred that said antigen-presenting vehicles which carry empty MHC Class I molecules are loaded with an antigen-derived T-cell-immunogenic MHC Class I-binding peptide having from about 8 to about 11 amino acids.

Said culturing under specific CTL response-inducing conditions of T-lymphocytes comprising $CD8^+$ T-cell precursors is preferably carried out in the presence of both the peptide-loaded antigen-presenting vehicles and substances supporting said CTL response initiation culture.

In a specifically preferred embodiment of the invention, said antigen-specific CTL response is a primary CTL response induced in a naive T-lymphocyte culture.

In another specifically preferred embodiment of this invention, said CTL response is specific for an autologous antigen from which said T-cell immunogenic MHC Class I-binding peptide is derived.

This invention also covers a process of inducing an antigen-specific helper T-lymphocyte response in a T-lymphocyte culture, comprising the steps of loading antigen-presenting vehicles which carry empty MHC Class II molecules with an antigen-derived T-cell-immunogenic MHC Class II-binding peptide, culturing T-lymphocytes comprising $CD4^+$ T-cell precursors in the presence of the peptide-loaded antigen-presenting vehicles under specific helper T-lymphocyte response-inducing conditions, and, optionally, isolating an antigen-specific helper T-lymphocyte from the resulting culture and culturing said isolated helper T-lymphocyte.

In such a process, said antigen-presenting vehicles which carry empty MHC Class II molecules are preferably loaded with an antigen-derived T-cell-immunogenic MHC Class II-binding peptide having from about 10 to about 18 amino acids.

The invention further provides an antigen-specific T-lymphocyte obtained by the above process of inducing an antigen-specific T-lymphocyte response in a T-lymphocyte culture, comprising the steps of loading antigen-presenting vehicles which carry empty MHC molecules with an antigen-derived T-cell-immunogenic MHC-binding peptide, culturing T-lymphocytes in the presence of the peptide-loaded antigen-presenting vehicles under specific T-lymphocyte response-inducing conditions, isolating an antigen-specific T-lymphocyte from the resulting culture and culturing said isolated T-lymphocyte.

This invention also covers a pharmaceutical composition comprising an immunologically effective amount of an antigen-specific T-lymphocyte and a carrier, diluent or adjuvant therefor, said antigen-specific T-lymphocyte being obtained by the above process of inducing an antigen-specific T-lymphocyte response in a T-lymphocyte culture, comprising the steps of loading antigen-presenting vehicles which carry empty MHC molecules with an antigen-derived T-cell-immunogenic MHC-binding peptide, culturing T-lymphocytes in the presence of the peptide-loaded antigen-presenting vehicles under specific T-lymphocyte response-inducing conditions, and, optionally, isolating an antigen-specific T-lymphocyte from the resulting culture and culturing said isolated T-lymphocyte.

In addition, the invention covers a pharmaceutical composition comprising an immunologically effective amount of an antigen-derived T-cell-immunogenic MHC-binding peptide and a carrier, diluent or adjuvant therefor, wherein said antigen-derived T-cell-immunogenic MHC-binding peptide is capable of inducing an antigen-specific T-lymphocyte response in the above process comprising the steps of loading antigen-presenting vehicles which carry empty MHC molecules with the antigen-derived T-cell-immunogenic MHC-binding peptide, and culturing T-lymphocytes in the presence of the peptide-loaded antigen-presenting vehicles under specific T-lymphocyte response-inducing conditions.

As indicated before, the invention also provides a process of identifying T-cell-immunogenic peptides in a group of candidate peptides, comprising the steps of synthesizing the candidate peptides, testing which of these candidate peptides is capable of binding to empty MHC molecules carried by antigen-presenting vehicles, and testing which of the MHC-binding peptides is capable of inducing a peptide-specific T-lymphocyte response in a T-lymphocyte culture.

Preferably, said antigen-presenting vehicles which carry empty MHC molecules comprise antigen-presenting cells having an antigen-processing defect, such as murine RMA-S cells or human 174.CEM T2 cells.

DETAILED DESCRIPTION OF THE INVENTION

The present invention provides methodology to induce primary MHC-binding peptide-specific cytotoxic T lymphocyte responses, thus bypassing the need for in vivo immunization.

The method is based on the use of antigen presenting cells that express "empty" MHC class I molecules due to an antigen processing defect that precludes loading of MHC class I molecules with endogenous peptides. As a result these APC can be efficiently loaded with a single exogenous MHC class I binding peptide of choice. Addition of human β2-microglobulin augments the expression of peptide loaded MHC molecules and improves primary CTL response induction.

These exogenous peptide-loaded cells in contrast to peptide-loaded parental cells without the processing defect are capable of primary CTL response induction. The invention includes all methodologies to induce primary T cell responses with responding lymphocyte populations from non-immunized "naive" individuals that are based on the principle of more efficient peptide-presentation utilizing exogenous peptide-filled MHC molecules.

This methodology allows identification of MHC binding peptides capable of T cell response induction against both foreign and autologous peptides, entirely by in vitro procedures.

1. Antigen processing defective cell lines and other empty MHC molecule bearing antigen presenting vehicles suitable to induce primary T cell responses The invention utilizes processing defective cell lines of mammalian origin. These cell lines have a defect in one of the cellular gene products responsible for peptide transport into the subcellular compartment where peptide loading into MHC class I or MHC class II molecules takes place. The prototype processing defective cell lines are RMA-S of murine origin (15, 18) and 174.CEM T2 of human origin (20). The processing defect does not need to be complete, as long as an unusually large proportion of cell surface MHC class I (or class II) molecules is devoid of endogenously processed peptide. The 174.CEM T2 cell line for example has signal peptides bound to its cell surface MHC class I molecules that can apparently cross from the cytoplasm into the endoplasmic reticulum despite the processing defect (21). Likewise the antigen processing defect in RMA-S cells is not complete (23, 24). Still, both cell lines, in contrast to their parental counterparts, are capable of primary CTL response induction, when appropriately loaded with MHC class I binding immunogenic peptides. In the case of RMA-S the processing defect is located in the HAM-2 gene located within the MHC class II region. Transfection of the intact HAM 2 gene or its rat analogue MTP-2 restores processing by RMA-S of endogenous peptides (19, 24). It is likely that the 174.CEM T2 line has a very similar processing defect as a result of a large deletion in the HLA class II region, including the human analogues of HAM 1 and 2, as well as a proteasome-encoding region that may be involved in the generation of cytoplasmic peptides from proteins.

The basic principle of the invention is expression in processing defective cells of empty MHC class I or class II molecules that can be loaded with exogenous (i.e. added from the outside) immunogenic peptides and which can serve as a highly efficient vehicle for antigen presentation. Therefore the invention is extended to all antigen presenting lipid bilayer carrying vehicles incorporating empty MHC molecules that can be loaded with exogenous peptides. This includes all animal, plant, insect or other cells carrying native or foreign empty MHC molecules or artificial lipid bilayer systems carrying empty MHC molecules such as liposomes incorporating empty MHC molecules. The invention comprises presentation of peptides bound to MHC class I molecules to CD8+ T-cell precursors as well as presentation of peptides bound to MHC class II molecules to CD4+ T cell precursors.

2. Loading of empty MHC molecules on processing defective cell lines and other empty MHC molecule bearing antigen-presenting vehicles with exogenous immunogenic peptides Processing defective cell lines and said empty MHC molecule bearing antigen-presenting vehicles are loaded with exogenous immunogenic peptides of defined length (8–11 amino acids for MHC class I loading; approximately 10–18 amino acids for MHC class II loading) in serum free medium. To prevent rapid degradation of MHC molecules the temperature during incubation with MHC binding peptide may be lowered to 20–30 degrees Centigrade. In the case of peptide loading of the MHC class I molecules on the murine processing defective cell line RMA-S, this decrease in temperature during peptide loading is advantageous to achieve an optimal level of peptide loaded MHC class I at the cell surface (9). In the case of the human cell line 174.CEM.T2 decrease in temperature does not improve the level of peptide bound to MHC class I molecules.

Addition of human β2-microglobulin further enhances peptide-loaded MHC Class I expression on both murine RMA-S cells and human 174.CEM T2 cells. Subsequent primary CTL response induction is also enhanced.

Once peptide has bound to MHC molecules these molecules are stabilized. This results in increased cell surface expression of MHC molecules, largely filled with a unique immunogenic peptide of choice.

The peptide loaded cells are now ready for antigen presentation to T lymphocytes in cultures at 37° C. To improve subsequent antigen presentation the processing defective cell lines or said noncellular antigen presenting vehicles can be equipped with additional molecules that can serve as costimulatory signals for T cell response initiation such as the B7 molecule (ligand for CD28 in T cells), accessory molecules such as ICAM-1 or ICAM-2 (ligands for LFA-1 on T cells), or any other molecule that further promotes the efficiency of T cell response initiation. Expression of these costimulatory molecules is achieved by transfection in the case of processing defective cell lines or by biochemical procedures in the case of noncellular antigen presenting vehicles, such as incorporation of purified accessory molecules.

3. Cell culture for induction of primary T cell responses with peptide loaded processing defective cell lines or other peptide loaded antigen presenting vehicles and responding lymphocytes from naive individuals Lymphocytes from non-immunized individuals are cocultured with peptide-loaded processing defective cells or other empty MHC molecule bearing antigen presenting vehicles at 37° C. for a sufficient length of time to expand a small number of specific antigen responsive precursor cells. Once the T cell response is initiated, the cultures may be restimulated in various ways, including peptide presentation on antigen presenting cells without processing defect. Alternatively, if the response is strong enough to measure a specific T cell response, the cultures need not be restimulated.

Media to support the response initiation cultures may be serum-free or serum-containing and may or may not contain extra cytokines or other supplements.

4. Source of peptides capable of T cell response induction

Peptides used for T cell response initiation can be foreign peptides derived from the sequence of e.g. infectious agents or autologous peptides. Response initiation against foreign peptides is important to identify target peptides of responses against infectious agents. Response initiation against autologous peptides is important for identification of target peptides for T cell based immune eradication of non-virus induced cancer or for identification of peptides recognized by T cells involved in autoimmune disease. We have shown that T cell response initiation is possible against immunodominant peptides using peptide loaded murine RMA-S antigen presenting cells ((9) and example 1). We have also proven that T cell response initiation against an autologous peptide of the p53 tumor suppressor molecule is possible with p53 peptide loaded 174.CEM.T2 antigen presenting cells (example 2).

EXAMPLE 1
Primary CTL response induction against Sendai or adenovirus peptides loaded into empty $K^b$ and $D^b$ MHC class I molecules, respectively, at the surface of processing defective RMA-S cells This example of primary CTL response induction has been published on 27 Nov. 1991 (9). An excerpt of this publication relevant to this patent application is given below.
Materials and methods
1. Mice C57BL/6 (B6, H-$2^b$) mice were bred in our institute under specific pathogen-free conditions. Notably the mice used in these experiments were free of Sendai virus and had never been in contact with Sendai virus as tested serologically in an ELISA.
2. Peptides Peptides were synthesized on a Biosearch (Millipore, Bedford, Mass.) 9500 peptide synthesizer according to Merrifield (25), dissolved in PBS or serum-free Iscove's modified Dulbecco's medium (IMDM, Flow Laboratories, Irvine, Scotland) and stored at −20° C. The Ad5 E1A peptide (A16: amino acid (aa) sequence 232–247) encompasses the immunodominant CTL epitope of adenovirus type 5 for H-$2D^b$ restricted CTL and was shown to be recognized by a CTL clone capable of eradicating adenovirus E1-induced tumors (26). A synthetic peptide (S16: sequence 321–336) containing the immuno-dominant CTL epitope of Sendai virus nucleoprotein for H-$2K^b$-restricted CTL(12) was used. Only the Sendai peptide of 9 aa (S9: aa sequence 234–332) is able to bind with high affinity to MHC class I molecules (4). This peptide is also present as a minor species in preparations of synthetic peptides larger than nine aa (4). The single letter code sequence of S16 is SEQ ID NO:1:HGEFAPGNYPALWSYA, the sequence of S9 is SEQ ID NO:2:FAPGNYPAL and the sequence of A16 is SEQ ID NO:3:CDSGPSNTPPEIHPW.
3. Induction of primary CTL responses RMA-S or RMA cells were pre-cultured for 36 h at 22° C. or 37° C. in IMDM medium supplemented with 2% human pooled serum, penicillin (100 IU/ml), kanamycin (100 µg/ml), S and 2-ME ($2\times10^{-5}$ M). The cells were irradiated at 7500 rad or mitomycin C treated (50 µg/ml) in serum-free medium, 2 h at 22° C.), washed three times and subsequently incubated for 4 h with or without synthetic peptides, A16 or S16 or S9, at 22° C. in serum-free IMDM medium. Without further washing these (peptide-loaded) RMA-S cells were incubated 1:1(v/v) with C57BL/6 nylon wool-passed spleen cells (B6 NWP SC) in 24-well culture plates: $4\times10^6$ responder cells and $1\times10^6$ stimulator cells in 1 ml of culture medium per well in IMDM medium supplemented with 10% FCS, penicillin (100 IU/ml), kanamycin (100 µg/ml), and 2-ME($2\times10^{-5}$M). For a primary CTL response NWP SC of non-immunized C57BL/6 mice were used.
4. Generation of peptide specific CTL clones Bulk CTL from primary Sendai NP peptide specific stimulated cultures as described under 3 were restimulated twice with peptide pulsed normal spleen cells. Subsequently Sendai peptide-specific CTL clones were obtained by limiting dilution procedures including the use of interleukin-2 rich medium to expand individual T cell clones (26). Several Sendai peptide specific CTL clones were obtained this way.

One clone investigated in detail had lytic ability against both peptide pulsed target cells and Sendai virus infected cells. Its activity against virus-infected target cells was indistinguishable from that of CTL clones generated from Sendai primed mice, with proven in vivo activity against virulent Sendai virus (27). Therefore this type of clone might be active in adoptive transfer protection experiments.
5. Induction of secondary CTL responses For secondary CTL responses NWP SC of C57BL/6 mice were used that were primed by one i.p. injection of $10^2$ hemagglutination units (HAU) of nonvirulent Sendai virus (lot 40340087, Flow Laboratories, stored at −7° C.) and used between 4 and 6 weeks after immunization as described (28).
6. Depletion of T cell subsets NWP SC were depleted for CD4$^+$ cells and MHC class II$^+$ cells by treament with anti-CD4 mAB (1:40 dilution of hybridoma cultures SN of SN 172.4, (14) and anti-I-A$^b$ mAB (1:1000 dilution of ascites fluid of B17/263 and C' and checked for efficacy by cytofluorimetry. In some experiments anti-I-A$^b$ mAB was present during the culture (1:1000 dilution of ascites fluid of B17/263). As a control the NWP SC were mock-treated with C' alone. For blocking of CTL responses by anti-CD8 mAb, the HPLC-purified antibody 53.6.7 was added in different final dilutions in the 5-day culture: 1:50, 1:500, 1:5000.
7. Cytotoxicity assays After 5 days of culture the effectors were harvested on a lymphoprep (Nycomed Pharma, Oslo, Norway) gradient and tested for cytotoxic function on 2000 $^{51}$Cr-labeled target cells ranging from E/T 50 to E/T 0.8 in twofold dilution steps. The percentage specific $^{51}$Cr release was calculated by the formula:

$$\frac{cpm \text{ experimental well} - \text{background } ^{51}\text{Cr release}}{cpm \text{ 2\% Triton X-100} - \text{background } ^{51}\text{Cr release}} \times 100$$

Background (medium) release was always <25% of maximal (2% Triton X-100) release. The SE of triplicate culture was always <5% specific $^{51}$Cr release. Cytolytic activity calculated from individual dose-response curves is expressed as lytic units per $10^6$ effector cells. Calculations were performed using linear regression. As target cells served: B6 mouse embryo cells, treated for 2 days with 50 U/ml IFN-γ at 37° C., LPS-induced (30 µg/ml LPS-B, Bacto Lab., Difco, Detroit, Mich., added to spleen cells for 5 days at 37° C.) B cell blasts from C57BL/6 mice (LPS) or EL4 cell (thymoma cell line of C57BL/6 origin, expressing $K^b$ and $D_b$). Target cells were incubated for 15–30 min with peptides at 50 µM A 16, 50 µM S16 or 10 µM S9 before adding them 1:1 (v/v) to effector cells at 37° C. for 6 h. Virus-infected target cells were prepared by incubating $10^7$ target cells with 300 HAU of nonvirulent Sendai virus in 1 ml of medium for 1 h or 12 h before labeling with $^{51}$Cr (28).
8. Direct peptide binding studies RMA and RMA-S cells were cultured for 36 h at 26° C. in Iscove's medium supplemented with 2% human pooled serum. The S9 peptide was iodinated by chloramine T-catalyzed iodination to a specific activity of approximately 50 Ci/mmol. Cells were incubated with $^{125}$I-labeled S9 peptide for 1–4 h at 26° C., washed three times with DMEM and lysed on ice in TRITON X-100 lysis buffer (10 mM) Tris, pH 7.8, 140 mM NaCl, 1% TRITON X-100, lysis buffer 1 mM PMSF, 1 µg/ml trypsin inhibitor, 30 mTIU/ml aprotinin). MHC class I molecules were immunoprecipitated using rabbit anti-H-$2^b$ serum (29). Class I-associated peptide was quantitated by γ-spectrometry. For determination of H-2 levels $10^6$ cells were iodinated using lactoperoxidasecatalyzed iodination. Subsequently cells were washed three times in PBS and lysed in TRITON X-100 lysis buffer. H-2 antigens were precipitated from equal amounts of trichloroacetic acid (TCA)-precipitable counts (30) using rabbit anti-H-$2^b$ serum (29). Immunoprecipitates were analysed by SDS-PAGE on 12% gels, and gels were exposed to Kodak (Rochester, N.Y.) X-AR5 (photographic film) films. Results were expressed in arbitrary units. One unit is defined as the level of cell surface H-2 per cell and peptide binding per cell, respectively on RMA cells.

Results

1. Induction of primary viral peptide-specific CTL responses with peptide-loaded RMA-S cells The 16-mer adenovirus peptide (A16) used in this experiment was shown to sensitize target cells for lysis by a CTL clone capable of eradicating adenovirus E1-induced tumors (26). The 16-mer Sendai virus peptide (S16) could sensitize target cells for lysis by specific H-$2K^b$-restricted CTL and induce protective immunity against a lethal Sendai virus infection in C57BL/6 mice (12). A16 and S16 peptides were incubated with 22° C. cultured RMA-S cells. Primary CTL responses could be induced by RMA-S cells loaded with these viral peptides. The responses were specific for the inducing adeno and Sendai peptides (FIG. 1).

2. Peptide concentration required for induction of primary CTL responses with peptide-loaded RMA-S cells and for target cell lysis by a primary CTL bulk induced by peptide-loaded RMA-S cells Recent studies have demonstrated that a Sendai peptide of 9aa, present as a minor species in preparations of synthetic peptides longer than 9 aa, binds with high affinity to the H-$2K^b$ MHC class I molecule (4). Peptide titration experiments showed that 50-fold lower concentrations of a 9-mer peptide than of a 16-mer peptide suffice for induction of a T cell response (FIG. 2A). The same peptide titration was performed for sensitization of target cells. The results indicate that target cell sensitization is accomplished with about a 1000-fold lower peptide concentration than required for in vitro response induction (FIG. 2B).

3. Peptide-loaded RMA-S but not RMA cells can induce a specific primary CTL response We examined the presenting capacity of RMA-S cells and the parental cell line RMA after incubation with S9 peptide in primary CTL responses (FIG. 3A). A primary response was obtained only by stimulation of T cells with peptide-loaded RMA-S cells (FIG. 3A). About 100-fold lower peptide concentration was required when the RMA-S cells were pre-cultured at reduced temperature (22° C.) than at 37° C. (FIG. 3B), corresponding with a similar temperature dependence of MHC class I expression (FIG. 4A and B). RMA cells incubated with peptides at any concentration were non-stimulatory at either temperature (FIG. 3A).

4. Primary peptide-specific CTL are cross-reactive on virus-infected cells

Primary CTL responses induced with Sendai peptide-loaded RMA-S cells were Sendai peptide specific (FIG. 1) and $K^b$ restricted (data not shown) and could lyse target cells expressing the antigenic determinant endogenously following virus infection (FIG. 3A and B). Lysis of the target cells infected with Sendai virus was dependent on the time of exposure to the virus. Target cells that were incubated with Sendai virus for 12 h were equally lysed as peptide-loaded target cells, whereas 1 h infected target cells were only half-maximally lysed compared to peptide-loaded target cells (FIG. 3B). This is not unexpected, since a longer infection time allows more viral epitopes to be presented by MHC class I molecules.

5. Specific secondary CTL responses generated by both peptide-loaded RMA and peptide-loaded RMA-S cells In contrast to primary CTL responses, secondary responses were obtained with both peptide-loaded RMA-S and RMA cells (FIG. 3C). Higher levels of response were measured when RMA and RMA-S cells were precultured at 22° C. to increase MHC class I expression (FIG. 3C). Sendai virus-infected RMA-S cells, in contrast to Sendai-virus infected RMA cells, did not induce a secondary CTL response (data not shown), in agreement with the notion that RMA-S cells have a defect in antigen presention via the endogenous pathway (18, 31).

6. Temperature dependence of MHC class I expression on RMA-S cells compared to RMA cells A similar expression pattern of Thy-1, CD45, LFA-1α, LFA-1β and ICAM-1 is observed for RMA and RMA-S cells (9). Expression of MHC class II molecules, B cell and monocyte/macrophage-specific markers is not demonstrable, nor of CD4 and CD8 (9). RMA and RMA-S cells differ only for MHC class I ($K^b$ and $D^b$) cell surface expression (9). Thus, none of the measured cells surface markers is altered by the selection of the RMA-S cell line with the exception of the molecule that was selected for, i.e. MHC molecules. Moreover, of all markers tested only MHC class I expression on RMA-S and on RMA cells is strongly temperature dependent (9).

7. Relative levels of H-2 complexes and peptide binding on RMA and RMA-S cells

To investigate further the difference in MHC/peptide expression between RMA and RMA-S cells, direct binding of S9 peptide to class I molecules on these cells was measured in relation to H-2 cell surface expression (FIG. 4A and B). Comparable binding of peptide onto RMA (26° C.) and RMA-S (26° C.) is observed with 1 µM S9 peptide and 1 nM S9 peptide, respectively (FIG. 4A). Even at 20 µM the amount of peptide bound to RMA cells did not reach the amount of peptide bount to RMA-S cells observed at 1 µM (not shown), a minimally required concentration for primary response induction by peptide-loaded RMA-S cells (FIG. 3A and B). Thus, RMA cells did not bind a comparable amount of peptide observed with RMA-S cells under conditions of primary response induction, not even at high peptide concentrations. Although peptide binding per cell on RMA and RMA-S cells only differs 2.5-fold, peptide binding expressed per H-2 molecule on RMA-S cells is tenfold higher than on RMA-cells (FIG. 4B). This shows the selective loading of MHC molecules on RMA-S with the exogenous peptide offered.

8. CD4 cell- and MHC class II cell-independence of primary peptide-specific CTL responses induced by peptide-loaded RMA-S cells Removal of $CD4^+$ and class $II^+$ cells from the responder population does not diminish the CTL activity generated with peptide-loaded RMA-S cells (FIG. 5). Thus, primary responses induced by peptide-loaded RMA-S cells were completely $CD4^+$ $T_h$ cell and class II independent.

9. CD8 dependence of primary CTL responses induced by peptide-loaded RMA-S cells The primary CTL induction by peptide-loaded RMA-S cells can be blocked completely in the presence of anti-CD8 mAb in the culture (FIG. 6). Also, at target cell level, the effector function of a primary CTL bulk was blocked with anti-CD8 mAb (data not shown).

Comment

For an extensive discussion of these results see (9). This example shows successful induction of primary peptide-specific CTL responses in vitro utilizing the unique characterics of the RMA-S cell line as a stimulator cell. The resulting CTL responses are peptide specific (FIG. 1) and can lyse virus-infected target cells (FIG. 3A and 3B). Peptide titration experiments show that lower concentrations of peptide are required when the peptide of optimal length is used (FIG. 2A and B), consistent with the idea that only exogenous peptides of optimal length bind efficiently to the MHC class I molecules and are present in small amounts in preparations of longer peptides. The results also indicate that target cell sensitization (FIG. 2B) is accomplished with much lower doses of peptide than required for in vitro response induction (FIG. 2A).

Whereas the RMA-S cell line is a good inducer of primary CTL responses in vitro, its parental cell line RMA is not (FIG. 3A and 3B). RMA and RMA-S have thus far been found to differ only in cell surface expression of MHC class I molecules, the property for which RMA-S was selected. When co-stimulatory activity of RMA-S cells was tested by addition of unloaded RMA-S cells to cultures of peptide-loaded RMA cells no primary CTL response developed (data not shown). Thus, the likelihood of only a single relevant difference (MHC class I expression) between RMA and RMA-S cells and the assay on co-stimulatory activity do not support the notion of increased co-stimulatory activity exerted by RMA-S in comparison with RMA. A primary response induction can be established at lower peptide concentrations when RMA-S cells were precultured at 22° C. compared to 37° C. (FIG. 3A and B). None of the cell surface markers tested other than MHC class I exhibits a temperature-dependent expression (FIG. 4A and B). The enhanced expression of empty MHC molecules at the surface of RMA-S cells at low temperature apparently facilitates the induction of primary CTL responses (FIG. 3A and B), compatible with a direct correlation between the number of specifically peptide-loaded MHC class I molecules at the cell surface and primary response induction.

Secondary CTL responses were induced with both peptide-loaded RMA-S and RMA cells with lytic capacities dependent on the pre-incubation temperature of the stimulator cells (FIG. 3C). More empty MHC class I molecules appear at the cell surface of RMA-S and RMA cells at low temperature that can be stabilized by exogeneous MHC-binding peptides.

The amount of peptide bound to RMA-S cells on a per cell basis is 2.5-fold higher than on RMA cells (FIG. 4B). The level of peptide binding on RMA-S cells at a concentration that will induce primary CTL responses, cannot be achieved on RMA cells, not even at high concentrations (FIG. 4A and data not shown). Although a 2.5-fold difference does not seem large, it might favor the notion of a threshold level and/or density of relevant MHC/peptide complexes at the cell surface of the APC for induction of a T cell response. Another consideration is the efficient loading of empty MHC molecules on RMA-S cells (FIG. 4B) and the CD8 dependence of primary CTL responses induced by peptide-loaded RMA-S cells (FIG. 6). MHC molecules filled with irrelevant peptides are predicted to be largely absent from RMA-S cells, whereas the majority of MHC molecules on RMA contain irrelevant peptides. Consequently, the TcR and CD8 molecules on the CTL precursors are more likely to encounter the relevant MHC/peptide complex on RMA-S than on RMA cells. TcR and CD8 on the CTL must interact with the same class I molecule (10, 11). MHC class I molecules, whether they are filled with relevant or irrelevant peptide, serve as ligands for the CD8 molecule. Therefore, class I molecules that are occupied with irrelevant peptides may interfere in the interaction of CD8 with relevant MHC/peptide complexes and therefore prevent triggering of specific CTL in vivo.

Removal of $CD4^+$ and class $II^+$ cells from the responder population did not diminish the CTL activity generated with peptide-loaded RMA-S cells (FIG. 5). Thus, primary responses induced by peptide-loaded RMA-S cells are completely $CD4^+ T_h$ cell and class II independent. The peptides used in this study are presented by class I molecules and exclusively stimulate $CD8^+$ CTL precursors. We postulate that $CD8^+$ CTL are triggered by peptide-loaded RMA-S cells to produce their own IL-2, thereby circumventing dependence on $CD4^+ T_h$ cells or exogeneous IL-2.

A variety of other cell types was tested for their capacity of inducing primary virus-specific CTL responses (data not shown). The only other cells, in addition of RMA-S cells, reported to be capable of inducing primary peptide-specific CTL responses are dendritic cells (M. L. H. de Bruijn, J. D. Nieland, W. M. Kast and C. J. M. Melief, manuscript submitted). However, dendritic cells can only be obtained in low numbers after laborious isolation procedures and so far have withstood attempts to continuously grow them as lines. Dendritic cells may have the capacity to stimulate primary CTL responses by different mechanisms such as their extremely large surface area, adhesive properties and low occupancy of cell surface glycans with sialic acids.

EXAMPLE 2

Primary CTL response induction against autologous p53 tumor suppressor peptide loaded into empty HLA-A2.1 MHC class I molecules at the surface of 174CEM.T2 processing defective cells Methods 1. Blood donors Blood donors were normal healthy blood donors expressing the HLA-A2.1 allele upon routine NIH microcytotoxicity HLA typing.

2. Responder cells

Responder T cells are included in mononuclear white blood cells (PBL) of an HLA-A2.1 positive healthy donor. The PBL were separated from a buffycoat by Ficoll procedure (Lymphoprep of Nycomed-pharma, Oslo, Norway, cat. no. 105033) and washed two times in RPMI 1640 (Gibco Paislan, Scotland, cat. no. 041-02409) supplemented with 30% pooled human serum (tested for its capacity to support mixed lymphocyte cultures), 2 mM glutamine (ICN Biochemicals, Inc., Costa Mesa, Calif., U.S.A., cat. no. 15-801-55), penicillin (100 IU/ml, Brocades Pharma, Leiderdorp, The Netherlands), kanamycin (100 µg/ml, Sigma, St. Louis, Mo., U.S.A.).

3. p53 Peptide

A p53 peptide from the normal nonmutated p53 sequence with strong ability to bind to HLA-A2.1 by the assay described under Methods 4 was used for primary CTL response induction by peptide presentation on processing defective 174CEM.T2 cells. The sequence of this peptide is SEQ ID NO:4:LLGRNSFEV. This peptide had a free carboxy terminus and was synthesized on a Biosearch (Millipore, Bedford, Mass., U.S.A.) 9500 peptide synthesizer according to Merrifield (25), dissolved in PBS or serum-free Iscove's modified Dulbecco's medium (IMDM, Flow Laboratories, Irvine, Scotland) and stored at −20° C.

4. Peptide binding to HLA-A2.1

(174.CEM) T2 cells were washed twice in culture medium without FCS and put at a density of $2 \times 10^6$ cells/ml in serum free culture medium. Of this suspension 40 µl was put into a V bottomed 96 well plate (Greiner GmbH, Frickenhausen, Germany: 651101) together with 10 µl of the individual peptide dilutions (of 1 mg/ml). The end concentration is 200 µg/ml peptide with $8\times10^4$ (174.CEM) T2 cells. This solution was gently agitated for 3 min after which an incubation time of 16 hours at 37° C., 5% $CO_2$ in humified air took place. Then cells were washed once with 100 µl 0.9% NaCl, 0.5% bovine serum albumin (Sigma St. Louis, U.S.A.:A-7409), 0.02% $NaN_3$ (Merck Darmstadt, Germany:822335). After a centrifuge round of 1200 rpm the pellet was resuspended in 50 µl of saturating amounts of HLA-A2.1 specific mouse monoclonal antibody BB7.2 for 30 minutes at 4° C. Then cells were washed twice and incubated for 30 minutes with $F(ab)_2$ fragments of goat anti-mouse IgG that had been conjugated with fluoresceine isothiocyanate (Tago Inc Burlingame, Calif., U.S.A.:4350) in a dilution of 1:40 and a total volume of 25 µl.

After the last incubation, cells were washed twice and fluorescence was measured at 488 nanometer on a FACScan flowcytometer (Beeton Dickinson, Franklin Lakes, N.J., U.S.A.).

Markedly increased immunofluorescence indicates binding to HLA-A2.1.

5. Induction of primary CTL response

174CEM.T2 (T2) cells in a concentration of $2\times10^6$ per ml were incubated for 13 hours at 37° C. in a T25 flask (Falcon, Becton & Dickinson, Plymouth, England, cat. no. 3013) in serum-free Iscove's medium (Biochrom KG, Seromed, Berlin, Gemany, cat. no. F0465) with glutamine (2 mM, ICN Biochemicals Inc., Costa Mes, Calif., U.S.A., cat. no. 15-801-55) and antibiotics as mentioned under 2 and p53 peptide at a final concentration of 80 µg/ml. Subsequently the T2 cells were spun down and treated at a density of $20\times10^6$ cells/ml with Mitomycin C (final concentration 50 µg/ml) in serum-free RPMI 1640 (manufacturer see 2) medium during one hour at 37° C. Thereafter the T2 cells were washed three times im RPMI 1640. Primary CTL responses were induced by filling all wells of a 96-well-U-bottom plate (Costar, Cambridge, Mass., U.S.A., cat. no. 3799) with $1\times10^5$ Mitomycin-C treated T2 cells in 50 µl of medium (serum-free RPMI 1640 containing glutamine and antibiotics as mentioned before), containing peptide at a concentration of 80 µg/ml. To these stimulator cells were added $4\times10^5$ HLA-A2.1 positive PBL in 50 µl of medium to each well. Stimulator and responder cells were cocultured for 7 days at 37° C. in an humidified incubator (90% humidity) and 5% $CO_2$ in air.

6. Cytotoxicity assay

As target cells served T2 cells, labeled with 100 µCi $^{51}$Cr for 1 h at 37° C. After labeling the cells were washed twice with serum-free Iscove's medium, and then incubated for 60–90 minutes with peptides at 20 µg/ml in a cell concentration of $2\times10^6$ cells per ml in serumfree Iscove's medium. The target cells were washed once more before adding them to the effector cells. Effector target ratio ranged from 20:1 to 2.5:1 in twofold dilution. Cytotoxicity function was tested on 2000 target cells per well in total volume of 100 µl RPMI containing 4% FCS and peptide at a concentration of 20 µg/ml per well. Total duration of the incubation time was 4 h at 37° C.

The percentage $^{51}$Cr release was calculated by the formula:

$$\frac{cpm \text{ experimental well} - \text{background } ^{51}\text{Cr release}}{cpm \text{ 2\% Triton X-100} - \text{background } ^{51}\text{Cr release}}$$

7. Cloning of CTL by limiting dilution

On days 7 and 14 after primary response induction (see 5) the PBL (responder cells) were restimulated with peptide. To this purpose all cells were harvested. Viable cells were isolated by Ficoll-procedure and washed in RPMI 1640. In a new 96-well-U-bottom plate 50,000 of these viable cells were seeded to each well together with µl medium I (RPMI (Gibco Paislan, Scotland cat. no. 041-02409)), 15% pooled human serum, glutamine and antibodies as described. Per well 20,000 autologous, irradiated (2500 rad) PBL and 10,000 autologous, irradiated (5000 rad) EBV transformed B lymphocytes were added together with 50 µl of medium II (RPMI (Gibco, Paislan, Scotland cat.no. 041-02409), 15% pooled human serum, glutamine and antibodies as described and peptide in a final concentration of 80 µg/ml. The cells were cultured for 7 days at 37° C. in an incubator with 5% $CO_2$ and 90% humidity.

On day 21 after primary response initiation, the cultured cells were harvested. Viable cells were isolated by Ficoll-procedure and washed in RPMI 1640. This bulk of viable cells was cloned by limiting dilution. Into each well of a new 96-well-U-bottom plate (Costar, Cambridge, cat. no. 3799) 50 µl medium I was added together with 100, 10, 1 or 0.3 viable cells.

To all the wells 20,000 pooled and irradiated (3000 rad) PBL of at least three different donors and 10,000 pooled and irradiated (10,000 rad) EBV transformed B-cells of at least two different HLA-A2.1 positive donors were added together with 50 µl of medium II, with peptide in a final concentration of 80 µg/ml, LEUCO-AGGLUTININ agoylutination assay in a concentration of 2%, human recombinant IL-2 in a concentration of 120 IU/ml (Eurocetus, Amsterdam).

8. Expansion of CTL clones

Individual wells of LD cultures were inspected regularly for cell growth. Cells from wells with expansive growth were transferred to larger culture volumes and repeatedly restimulated with irradiated PBL, HLA-A2.1 positive EBV B cells and p53 peptide as described under 7 and tested for cytotoxicity. Each CTL clone with peptide specific HLA-A2.1 restricted specificity was recloned at least once by the procedure outlined in section 7.

Results

1. Lytic activity of three HLA-A2.1 restricted CTL clones directed against autologous p53 peptide.

The specific cytotoxic activity of three CTL clones specifically generated against p53 peptide LLGRNSFEV (see SEQ ID NO.4) from PBL of a healthy donor by the procedures outlined in section 5, 7 and 8, is shown in Table 1.

TABLE 1

Lytic activity of three p53 peptide specific CTL clones generated following primary peptide driven CTL response initation

| | Percentage specific $^{51}$Cr release from target | | |
|---|---|---|---|
| | T2-A8 | T2-D6 | T2 |
| Clone C1 | | | |
| 20 | 62 | 0 | 0 |
| 10 | 95 | 0 | 5 |
| 5 | 79 | 0 | 0 |
| 2.5 | 70 | 0 | 1 |
| Clone D5 | | | |
| 20 | 85 | 0 | 12 |
| 10 | 100 | 0 | 21 |
| 5 | 89 | 6 | 12 |
| 2.5 | 100 | 0 | 19 |

TABLE 1-continued

Lytic activity of three p53 peptide specific CTL clones generated following primary peptide driven CTL response initation

| | Percentage specific $^{51}$Cr release from target | | |
|---|---|---|---|
| | T2-A8 | T2-D6 | T2 |
| Clone A5 | | | |
| 20 | 100 | 0 | 5 |
| 10 | 65 | 0 | 2 |
| 5 | 76 | 0 | 8 |
| 2.5 | 74 | 0 | 10 |

The CTL Clones C1, A5 and D5 were obtained following an induction of primary CTL responses in vitro with A8 peptide loaded T2 cells. The clones were tested for specificity on peptide loaded $^{51}$Cr labeled target cells ranging from E/T 20 to E/T 2.5 in twofold dilution steps.

A8 is a peptide of nine amino acids, derived from the wild type p53 protein. Peptide D6 is also derived from the wild type p53 sequence and is used as a negative control. Both peptides bind to the HLA-A2.1 molecule, as described in methods section 4.

Sequence in one letter codes for the two peptides: A8:SEQ ID NO:4:LLGRNSFEV; D6:SEQ ID NO:5:RMPEAAPPV. Peptide titration experiments showed that 20 ng/ml of the A8 peptide was sufficient for target cell sensitization. The concentration used in this test was 20 µg/ml.

The peptide-specificity clone only lysed HLA-A2.1 positive target cells incubated with p53 peptide and not HLA-A2.1 positive target cells not incubated with peptide or incubated with HLA-A2.1 binding irrelevant peptide. This result indicates that it is possible to generate a CTL response against an autologous peptide, in this case a peptide of the p53 tumor suppressor gene product, entirely by in vitro induction of response in PBL from a healthy non-immunized HLA-A2.1 positive donor.

Induction of primary CTL responses in vitro with peptide-loaded RMA-S cells. NWP SC of B6 unprimed mice were stimulated 1:1 (v/v) once in vitro with RMA-S cells, pre-cultured for 36 h at 22° C., only or incubated with 50 µM A16 peptide or 50 µM S16 peptide. Peptide was present during the 5-day culture at 25 µM concentration. The effectors were harvested and tested on B6 mouse embryo cells (MEC) and B6 LPS-induced B cell blasts (LPS) as target cells, without or with 50 µM A16 and S16, respectively.

FIG. 2A and B

Peptide titration at induction level (A) and at target level (B) of primary CTL induced by peptide-loaded RMA-S cells. NWP SC of B6 unprimed mice were stimulated once 1:1 (v/v) in vitro with RMA-S cells, pre-cultured for 36 h at 22° C., incubated with different concentrations of S9 and S16 Sendai peptides. The final peptide concentration is indicated in the figure (A). The effectors were harvested and tested on B6 mouse embryo cells with 10 µM S9 peptide. In (B) NWP SC of B6 unprimed mice were stimulated once 1:1 (v/v) in vitro with RMA-S cells, pre-cultured for 36 h at 22° C., incubated with 10 µM S9 peptide. The effector was harvested and tested on B6 mouse embryo cells with different concentrations of S9 and S16 Sendai peptides, as existed in the cytotoxicity assay.

FIG. 3A–D

Figure 1:
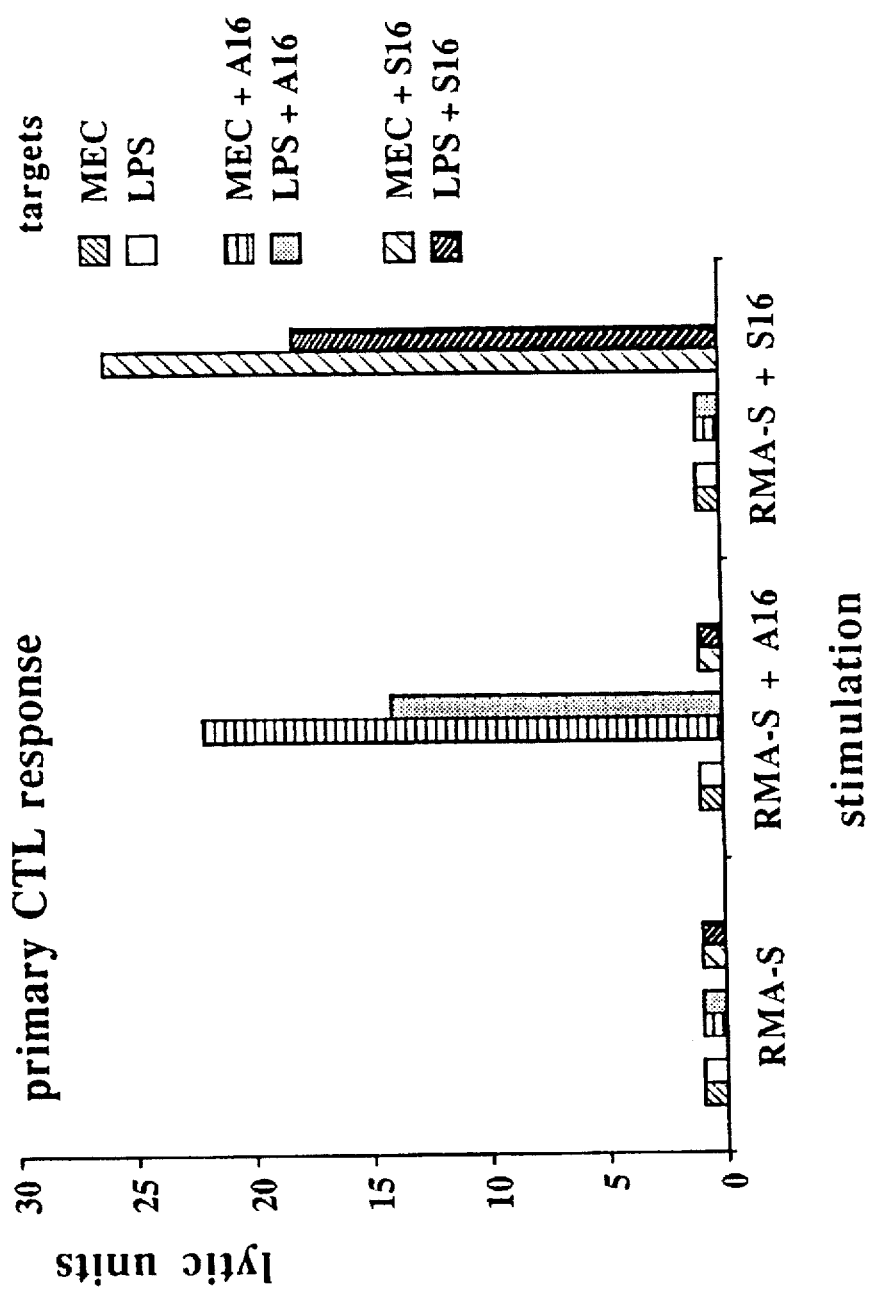
FIG. 1
Figure 2A:
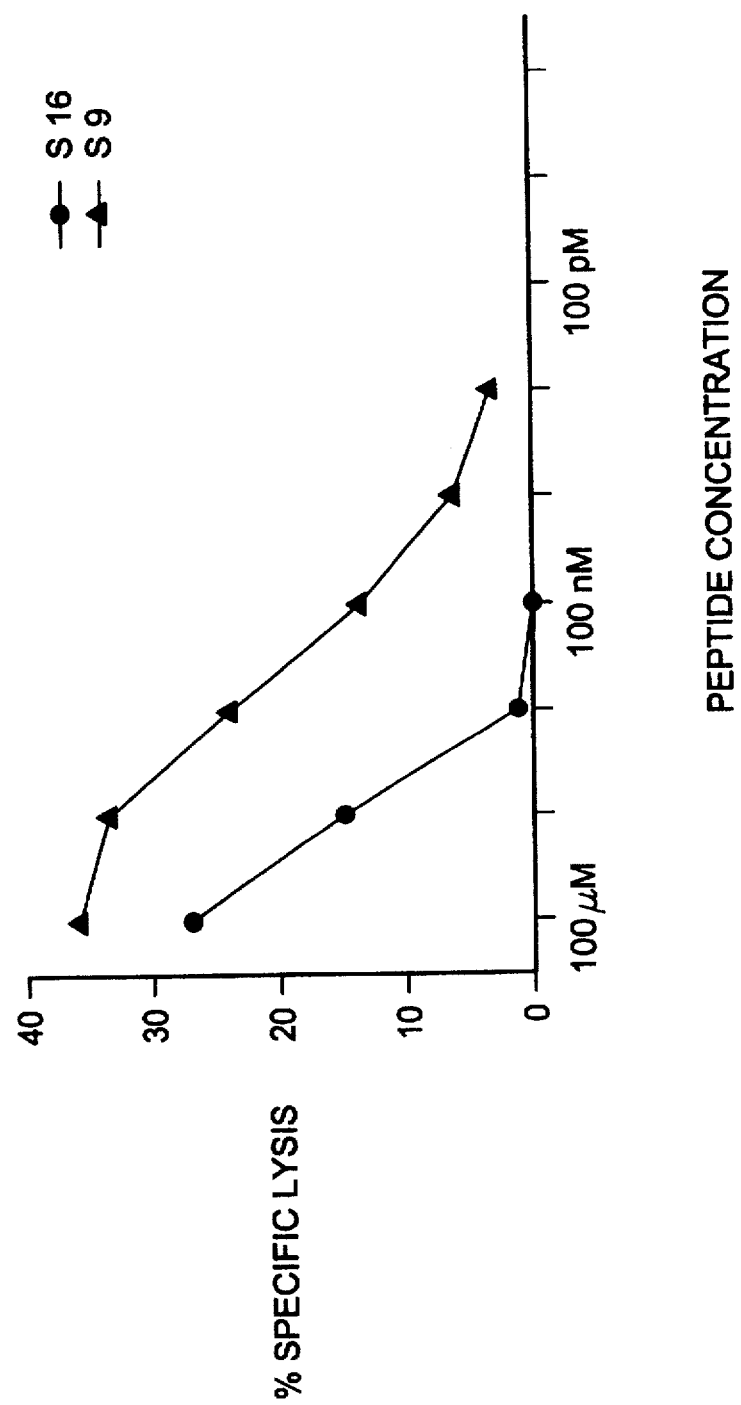
Figure 2B:
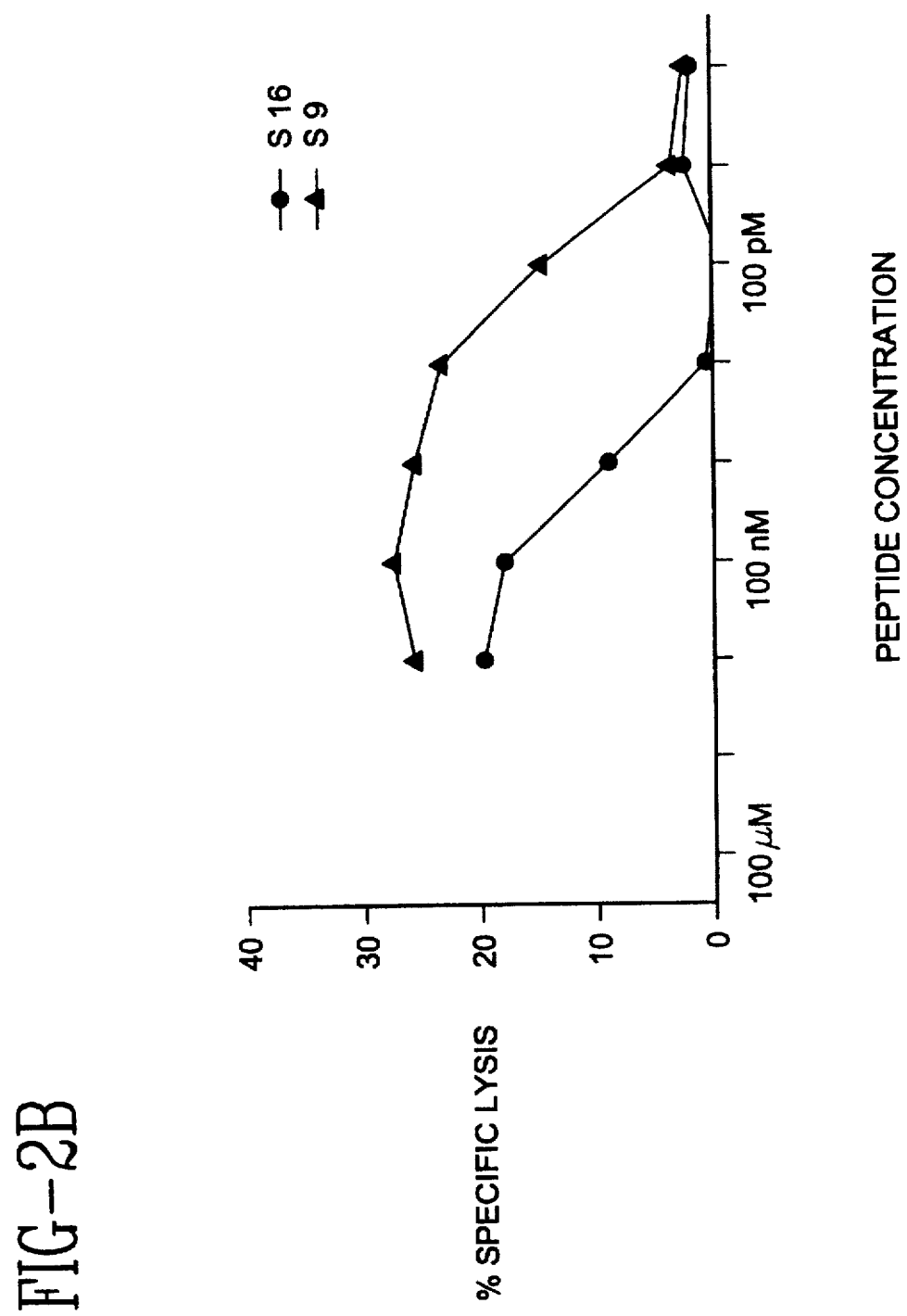
Figure 3D:
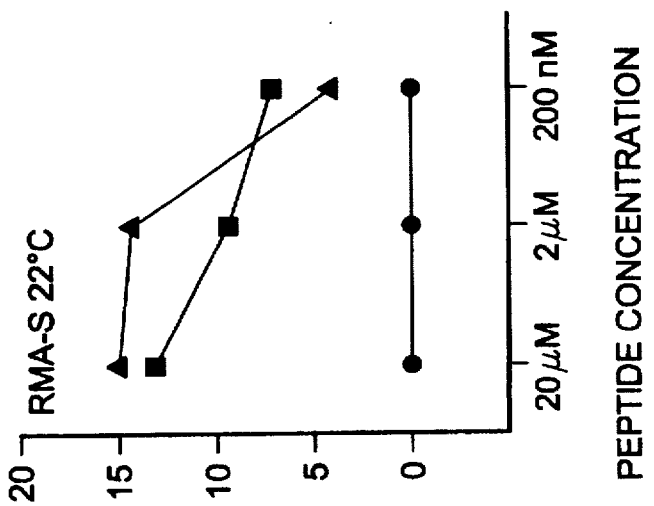
Figure 3C:
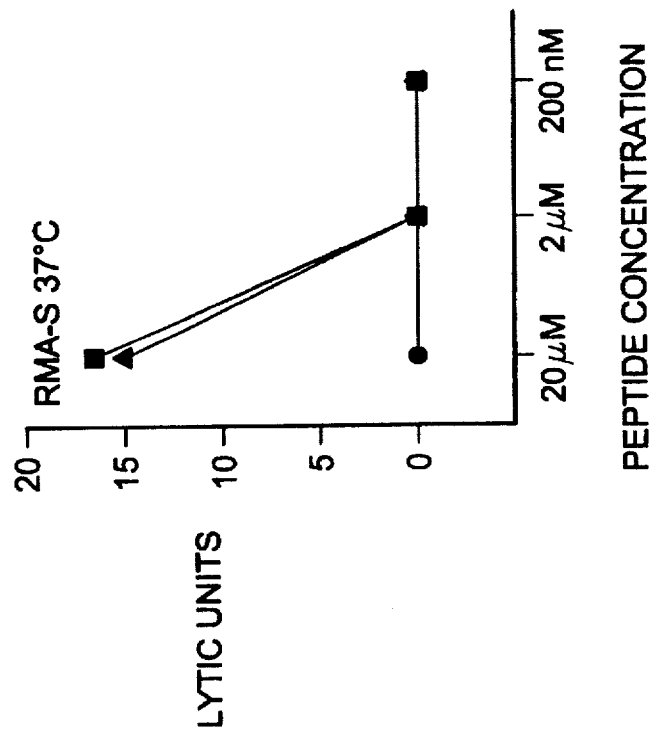
Figure 5:
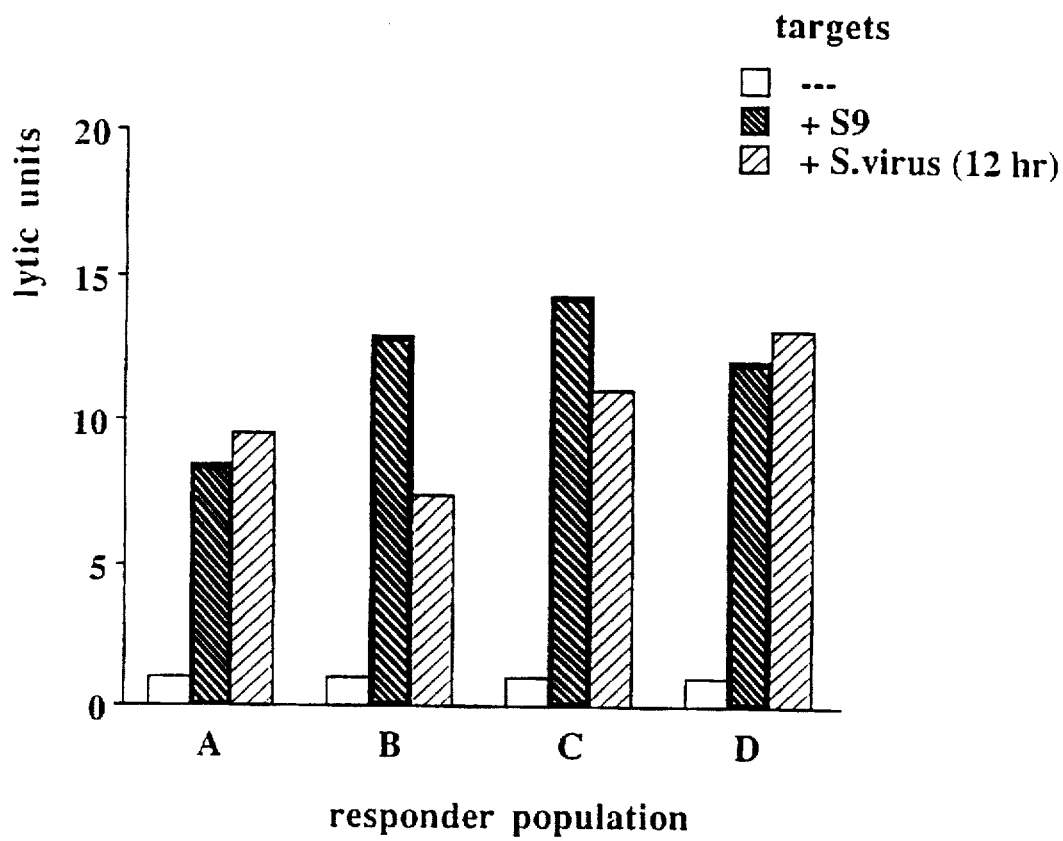
Figure 6:
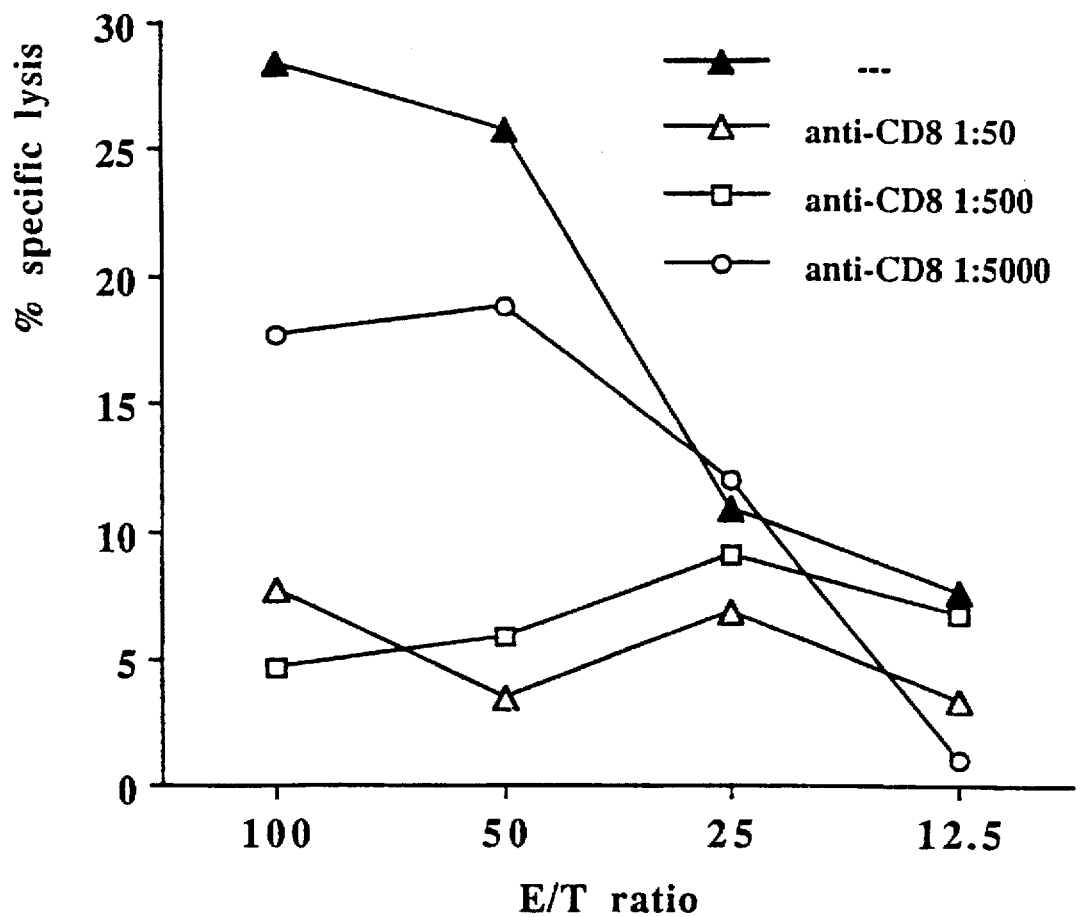

Primary and secondary CTL responses induced by peptide-loaded RMA-S cells. For primary CTL responses NWP SC of B6 unprimed mice were used (A and B). For secondary CTL responses NWP SC of B6 mice were primed once i.p. with non-virulent Sendai virus (C and D). Different concentrations of S9 peptide were used to load RMA-S and RMA cells that were pre-cultured at 37° C. or 22° C. Peptide-loaded RMA and RMA-S cells were cultured 1:1 (v/v) with B6 NWP SC for 5 days with a final peptide concentration as indicated in the FIG. 3A–D. EL4 cells were used as target cells without or with 10 µM S9 or infected with nonvirulent Sendai virus for 1 h or 12 h before labeling with $^{51}$Cr.

FIG. 4A and B

Direct peptide binding studies on RMA and RMA-S cells. RMA and RMA-S were cultured at 26° C. for 36 h. $^{125}$I-labeled S9 peptide (1 µM or 1 nM) was incubated at 26° C. for 4 h at 2.5×10$^6$ cells/ml in DMEM without serum. MHC class I molecules were immunoprecipitated using rabbit anti-H-2$^b$ serum. Class I-associated peptide was quantitated by γ-spectrometry. Results are means of duplicate experiments and shown in dpm after subtraction of normal serum control precipitates (A). In (B) 26° C. pre-cultured RMA and RMA-S cells were surface iodinated and H-2 antigens were precipitated from equal amounts of TCA-precipitable counts using rabbit anti-H-2$^b$ serum. The amount of cell surface H-2 on RMA-S cells is depicted relative to the amount on RMA-S cells, which is set at 1 arbitrary unit. Peptide binding was measured after 1 h of incubation at 26° C. with 700 nM $^{125}$I-labeled S9 peptide of 26° C. pre-cultured RMA and RMA-S cells and subsequent immunoprecipitation with anti-H-2$^b$ serum. The amount of class I-associated peptide on RMA-S cells is depicted relative to the amount on RMA-S cells, which is set at 1 arbitrary unit. Similar results were obtained in three independent experiments.

FIG. 5

Primary CTL responses induced by peptide-loaded RMA-S cells are CD4$^+$ cells- and class II$^+$ cell-independent. Responder cells were NWP SC of B6 unprimed mice (A) or NWP SC depleted for CD4$^+$ cells and class II$^+$ cells by anti-CD4 (SN 172.4) and anti-I-A$^b$ (B17/263) mAb and C' treatment (C, D). In (B) the NWP SC were mock-treated with C' alone. In (D) anti-I-A$^b$ mAb (B17/263) was present during the 5-day culture. These responder cells were stimulated once 1:1 (v/v) in vitro with 22° C. pre-cultured RMA-S cells incubated with 20 µM S9 peptide. The effectors were harvested and tested on EL4 target cells without or with 10 µM S9 peptide or infected with Sendai virus for 12 h before labeling with $^{51}$Cr. NWP SC and CD4$^+$ cell-depleted NWP SC were tested in the completely CD4$^+$ cell-dependent B6 anti-bm6 allospecific CTL response as previously described (32) (data not shown). Removal of CD4$^+$ cells from the responder population completely abolished the B6 anti-bm6 CTL response, indicating that the CD4$^+$ cells were functionally depleted (32).

FIG. 6

Primary CTL responses induced by peptide-loaded RMA-S cells are CD8 dependent. NWP SC of B6 unprimed mice were stimulated 1:1 (v/v) once in vitro with 22° C. pre-cultured RMA-S cells incubated with 20 µM S9 peptide in the absence or presence of different dilutions of anti-CD8 mAb (53.6.7), as indicated in the figure. After 5 days the effectors were harvested and tested on EL4 cells incubated with 10 µM S9 peptide.

References

1. B. A. Askonas, A. Mullbacher, R. B. Ashman. Cytotoxic T-memory cells in virus infection and the specificty of helper T cells. Immunology. 45: 79–84, 1982

2. G. van Bleek, S. G. Nathenson. Isolation of an endogenously processed immunodominant viral peptide from the class I H-2 K$^b$ molecule. Nature 348: 213–216, 1990

3. O. Rötzschke, K. Falk, K. Deres, H. Schild, M. Norda, J. Metzger, G. Jung, H. G. Rammensee. Isolation and analysis of naturally processed viral peptides as recognized by cytotoxic T cells. Nature 348: 252–254, 1990

4. T. N. M. Schumacher, M. H. L. de Bruijn, L. N. Vernie, W. M. Kast, C. J. M. Melief, J. J. Neefjes, H. L. Ploegh. Peptide selection by MHC class I molecules. Nature 350: 703–706, 1991

5. K. Falk, O. Rötzschke, S. Stevanovic, G. Jung, H. G. Rammensee. Allele specific motifs revealed by sequencing of self-peptides eluted from MHC molecules. Nature 351: 290–296, 1991

6. H. von Boehmer, W. Haas. Distinct Ir genes for helper and killer cells in the cytotoxic response to H-Y antigen. J. Exp. Med. 150: 1134–1142, 1979

7. L. P. de Waal, R. W. Melvold, C. J. M. Melief. Cytotoxic T lymphocyte non-responsiveness to the male antigen H-Y in the H-2D$^b$ mutants bm13 and bm14. J. Exp. Med. 158: 1537–1546, 1983

8. S. E. Macatonia, P. M. Taylor, S. C. Knight, B. A. Askonas. Primary stimulation by dendritic cells induces antiviral proliferation and cytotoxic T cell responses in vitro. J., Exp. Med. 169: 1255–1264, 1989

9. M. H. L. de Bruijn, T. N. M. Schumacher, J. D. Nieland, H. L. Ploegh, W. M. Kast, C. J. M. Melief. Peptide loading of empty major histocompatibility complex molecules on RMA-S cells allows the induction of primary cytotoxic T lymphocyte responses. Eur. J. Immunol. 21: 2963–2970, 1991

10. J. M. Connolly, T. H. Hauser, A. L. Ingold, T. A. Potter. Recognition by CD8 on cytotoxic T lymphocytes is ablated by several substitutions in the class I $\alpha$3 domain: CD8 and the T-cell receptor recognize the same class I molecule. Proc. Natl. Acad. Sci. U.S.A. 87: 2137–2141, 1990

11. R. D. Salter, R. J. Bejamin, P. K. Wesley, S. E. Buxton, C. Garret, T. P. J. Clayberger, A. M. Krensley, A. M. Normemt, D. T. Littman, P. Parkam. A binding site for the T cell co-receptor CD8 on the $\alpha$3 domain of HLA-A2. Nature 345: 41–46, 1990

12. W. M. Kast, L. Roux, J. Curren, H. J. J. Blom, A. C. Voordouw, R. H. Meloen, D. Kolakovsky, C. J. M. Melief. Protection against lethal Sendai virus infection by in vivo priming of virus-specific cytotoxic T lymphocytes with a free synthetic peptide. Proc. Natl. Acad. Sci. U.S.A. 88: 2283–2287, 1991

13. C. J. M. Melief. Tumor eradication by adoptive transfer of cytotoxic T lymphocytes. Adv. Cancer Res. 58: 143–175, 1992

14. W. M. Kast, C. J. M. Melief. In vivo efficacy of virus-derived peptides and virus-specific cytotoxic T lymphocytes. Immunol. Letters 30: 229–232, 1991

15. H. G. Ljunggren, K. Kärre. Host resistance directed selectively against H-2-deficient lymphoma virus. J. Exp. Med. 162: 1745–59, 1985

16. K. Kärre, H. G. Ljunggren, G. Piontek, R. Kiessling. Selective rejection of H-2-deficient lymphoma variants suggest alternative immune defence strategy. Nature 319: 675–678, 1986

17. H. G. Ljunggren, N.J. Stam, C. Öhlen, J. J. Neefjes, P. Hoglund, M.-T. Heemels, J. Bastin, T. N. M. Schumacher, A. Townsend, K. Kärre, H. L. Ploegh. Empty MHC class I molecules come out in the cold. Nature 346: 476–480, 1990

18. A. Townsend, C. Öhlen, J. Bastin, L. Foster, K. Kärre. Association of class I MHC heavy and light chains by viral peptide. Nature 340: 443–448, 1989

19. S. J. Powis, A. R. M. Townsend, E. V. Deverson, J. Bastin, G. W. Buther, J. C. Howard. Restoration of antigen presentation to the mutant cell line RMA-S by a MHC linked transporter. Nature 354: 528–531, 1991

20. R. D. Salter, P. Cresswell. Impaired assembly and transport of HLA-A and -B antigens in a mutant TXB cell hybrid. EMBO J. 5: 943–949, 1986

21. R. A. Henderson et al. HLA-A2.1 associated peptides from a mutant cell line: a second pathway of antigen presentation. Science 255: 1264, 1992

22. F. Esquivel, J. Yewdell, J. Bennink. RMA-S cells present endogeneously synthesized cytosolic proteins to class I-restricted cytotoxic T lymphocytes. J. Exp. Med. 175: 163–168, 1992

23. A. J. A. M. Sijts, M. H. L. de Bruijn, J. D. Nieland, W. M. Kast, C. J. M. Melief. Cytotoxic T lymphocytes against the antigen processing defective RMA-S tumor cell line. Eur. J. Immunol. in press 24. M. Attay, S. Jameson, C. K. Martinez, E. Hermel, C. Aldrich, J. Forman, K. Fisher Lindahl, M. J. Bevan, J. J. Monaco. HAM-2 corrects the class I antigen-processing defect in RMA-S cells. Nature 355: 647–649, 1992

25. R. B. Merrifield. Solid phase peptide synthesis. I. The synthesis of a tetra peptide. J. Am. Chem. Soc. 85: 2149–2154, 1963

26. W. M. Kast, R. Offringa, P. J. Peters, A. C. Voordouw, R. H. Meloen, A. J. van der Eb, C. J. M. Melief. Eradication of adenovirus E10induced tumors by E1A-specific cytotoxic T lymphocytes. Cell 59: 603–614, 1989

27. W. M. Kast, A. M. Bronkhorst, L. P. de Waal, C. J. M. Melief. Cooperation between cytotoxic and helper T lymphocytes in protection against Sendai virus infection. J. Exp. Med. 164: 723–738, 1986

28. L. P. de Waal, W. M. Kast, R. W. Melvold, C. J. M. Melief. Regulation of the cytotoxic T lymphocytes response against Sendai virus analyzed with H-2 mutants. J. Immunol. 130: 1090–1096, 1983

29. T. N. M. Schumacher, M.-T. Heemels, J. J. Neefjes, W. M. Kast, C. J. M. Melief, H. L. Ploegh. Direct binding of peptide to empty MHC class I molecules on intact cells and in vivo. Cell 62: 563–567, 1990

30. J. J. Neefjes, H. L. Ploegh. Allele and locus-specific differences in cell surface expression and the association of HLA class I heavy chain with $\beta$2-microglobulin: differential effects of inhibitions of glycosylation on class I subunit association. Eur. J. Immunol. 18: 801–810, 1988

31. T. Elliott, A. Townsend, V. Cerundolo. Naturally processed peptides. Nature 348: 195–197, 1990

32. C. J. P. Boog, J. Boes, C. J. M. Melief. Stimulation with dendritic cells decreases or obviates the CD4$^+$ helper cell requirement in cytotoxic T lymphocyte responses. Eur. J. Immunol. 18: 219–223, 1988

We claim:

1. A method of inducing in vitro antigen-specific cytotoxic T-lymphocytes in a T-lymphocyte culture, comprising the steps of:

(a) loading antigen-presenting vehicles consisting of processing-defective cell lines of mammalian origin that carry empty MHC Class I molecules with an antigen-derived T-cell-immunogenic MHC Class I-binding peptide to form MHC Class I-binding peptide-loaded antigen presenting vehicles; and (b) culturing naive T-lymphocyte precursors in the presence of the peptide-loaded antigen-presenting vehicles under specific CTL response-inducing conditions whereby a cytotoxic T-lymphocyte having an antigen specificity to the antigen-derived T-cell-immunogenic MHC Class I-binding peptide is formed.

2. The method of claim 1, further comprising isolating said cytotoxic T lymphocyte.

3. The method of claim 2, further comprising culturing said isolated cytotoxic T lymphocyte.

4. The method of claim 1, wherein said antigen-presenting vehicles which carry empty MHC Class I molecules simultaneously carry molecules which promote T-cell response initiation.

5. The method of claim 1, wherein said antigen-presenting vehicles which carry empty MHC Class I molecules are loaded with an antigen-derived T-cell immunogenic MHC Class I binding peptide having from about 8 to about 11 amino acids.

6. The method of claim 1, wherein said culturing under specific CTL-response-inducing conditions of $CD8^+$ T-lymphocyte precursors further comprises culturing said T-lymphocyte precursors in the presence of the peptide-loaded antigen-presenting vehicles and substances supporting CTL response initiation.

7. The method of claim 1, wherein said antigen-specific CTL response is a primary CTL response induced in a naive T-lymphocyte culture.

8. The method of claim 1, wherein said CTL response is specific for an autologous antigen from which said T-cell immunogenic MHC Class I binding peptide is derived.

9. A method of identifying a cytotoxic T-cell-immunogenic peptide comprising the steps of:

contacting a candidate peptide with an antigen-presenting vehicle, said antigen-presenting vehicle consisting of a cell line of mammalian origin that carries empty class I molecules, at a temperature and for a time sufficient for said candidate peptide to bind said antigen-presenting vehicle, wherein a peptide bound antigen-presenting vehicle is formed;

culturing naive T-lymphocytes in the presence of said peptide bound antigen-presenting vehicle;

and assaying for a cytotoxic T-lymphocyte having an antigen specificity for said candidate peptide, wherein the presence of a cytotoxic T-lymphocyte having said antigen specificity for said candidate peptide indicates said candidate peptide is a cytotoxic T cell-immunogenic peptide.

10. The method of claim 9, wherein said antigen presenting vehicle is an antigen presenting cell line having an antigen-processing defect.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 16 amino acids
        ( B ) TYPE: Amino Acid
        ( D ) TOPOLOGY: Linear ( x i ) SEQUENCE DESCRIPTION: SEQ ID NO:1:

His Gly Glu Phe Ala Pro Gly Asn Tyr Pro Ala Leu Trp Ser Tyr Ala
1               5                   10                  15

( 2 ) INFORMATION FOR SEQ ID NO:2:

( i ) SEQUENCE CHARACTERISTICS:
        ( A ) LENGTH: 9 amino acids
        ( B ) TYPE: Amino Acid
        ( D ) TOPOLOGY: Linear ( x i ) SEQUENCE DESCRIPTION: SEQ ID NO:2:

Phe Ala Pro Gly Asn Tyr Pro Ala Leu
1               5

( 2 ) INFORMATION FOR SEQ ID NO:3:

( i ) SEQUENCE CHARACTERISTICS:
        ( A ) LENGTH: 16 amino acids
        ( B ) TYPE: Amino Acids
        ( D ) TOPOLOGY: Liniar ( x i ) SEQUENCE DESCRIPTION: SEQ ID NO:3:

Cys Asp Ser Gly Pro Ser Asn Thr Pro Pro Glu Ile His Pro Val Val
1               5                   10                  15

( 2 ) INFORMATION FOR SEQ ID NO:4:

( i ) SEQUENCE CHARACTERISTICS:
        ( A ) LENGTH: 9 amino acids
        ( B ) TYPE: Amino Acid
        ( D ) TOPOLOGY: Linear ( x i ) SEQUENCE DESCRIPTION: SEQ ID NO:4:

Leu Leu Gly Arg Asn Ser Phe Glu Val
1               5

( 2 ) INFORMATION FOR SEQ ID NO:5:

( i ) SEQUENCE CHARACTERISTICS:
        ( A ) LENGTH: 9 amino acids
        ( B ) TYPE: Amino Acid
        ( D ) TOPOLOGY: Linear ( x i ) SEQUENCE DESCRIPTION: SEQ ID NO:5:

Arg Met Pro Glu Ala Ala Pro Pro Val
1               5